United States Patent [19]

Buononato et al.

[11] Patent Number: 5,309,577
[45] Date of Patent: May 10, 1994

[54] BUOYANT WRAP-AROUND SUNGLASSES

[76] Inventors: Guy S. Buononato, 6409 E. Pheasant La., Orange, Calif. 92669; Kemp F. Buononato, 310 N. Hickory Branch La., Orange, Calif. 92669; Thomas G. Buononato, 12691 Bonita Heights Dr., Santa Ana, Calif. 92705

[21] Appl. No.: 678,817

[22] Filed: Apr. 1, 1991

[51] Int. Cl.$^5$ .............................................. A61F 9/02
[52] U.S. Cl. ............................................ 2/452; 2/12; 2/432
[58] Field of Search ................... 2/452, 454, 439, 171, 2/209.3, 10, 12, DIG. 11; 351/43, 155, 158

[56] References Cited

U.S. PATENT DOCUMENTS

| | | | |
|---|---|---|---|
| 2,719,565 | 10/1955 | Wolff | 2/12 X |
| 4,621,378 | 11/1986 | Hatchman | 2/12 X |
| 4,768,231 | 9/1988 | Schrack | 351/158 X |
| 4,811,430 | 3/1989 | Janusz | 2/452 |
| 4,852,189 | 8/1989 | Duggan | 2/452 |
| 4,910,806 | 3/1990 | Baker et al. | 2/428 X |

FOREIGN PATENT DOCUMENTS 0612042 11/1948 United Kingdom .................... 2/454

Primary Examiner—Peter Nerbun
Attorney, Agent, or Firm—William L. Chapin

[57] ABSTRACT

An article of protective eye wear, specifically, sunglasses which are self-buoyant is disclosed. The self-buoyant sunglasses include an elongated flexible strap having two free ends provided with fasteners joinable together to form a band which encircles the head. The strap has a cutout section in its lower longitudinal edge wall for receiving an eye shield having the shape of a thin cylindrical plate. A flap formed in the upper edge of the strap folds down behind the strap to sandwich the upper margin of the eye shield, which is fastened to the strap and flap, preferably by strips coated on both sides with a pressure sensitive adhesive. In the preferred embodiment, the strap is made buoyant by fabricating it from a low-density polyethylene foam core, the outer surface of which core has adhered thereto by flame, heat and pressure, a nylon spandex cover.

19 Claims, 3 Drawing Sheets

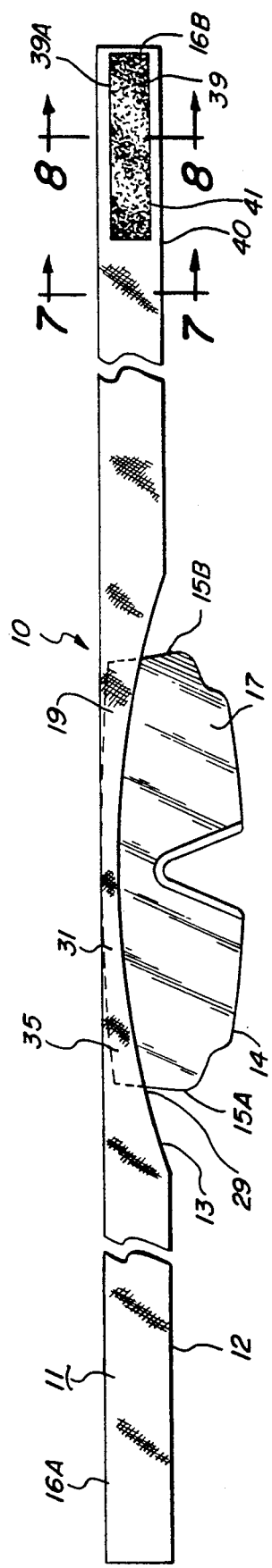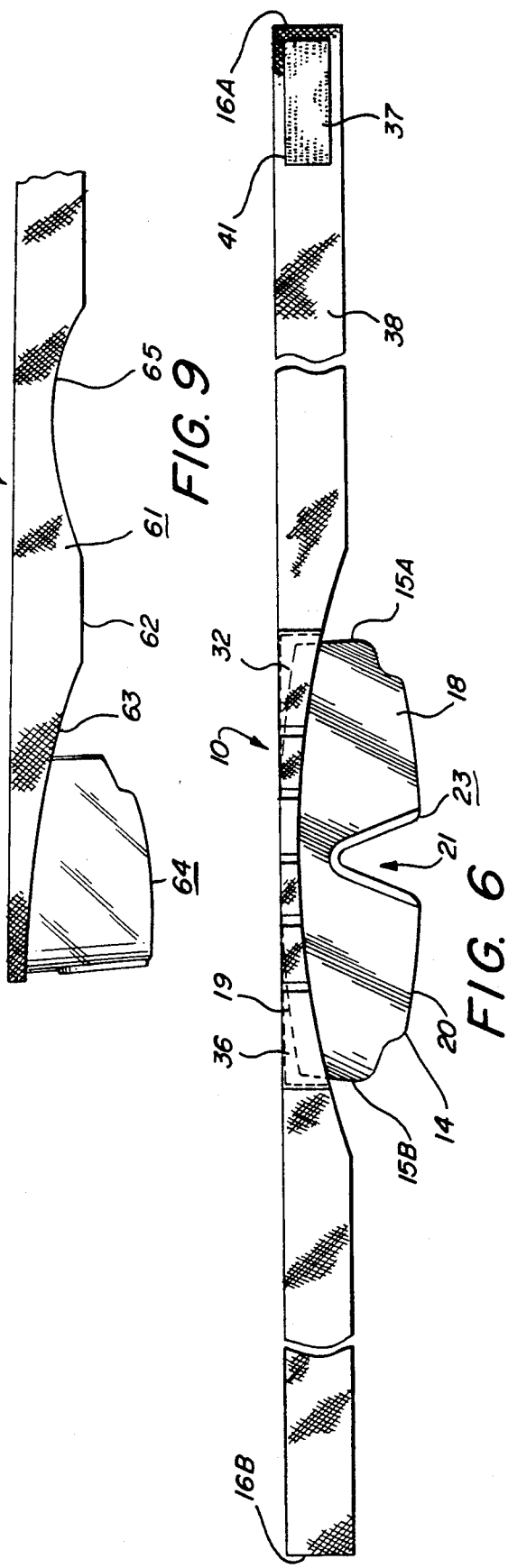

BUOYANT WRAP-AROUND SUNGLASSES

BACKGROUND OF THE INVENTION

A. Field of the Invention

The present invention relates to protective eye wear for people. More particularly, the invention relates to sunglasses of improved design which are buoyant.

B. Description of Background Art

Sunglasses are being worn by ever increasing numbers of people, who have been made aware of the damages of prolonged exposure of the eyes to ultraviolet rays emanating from the sun.

The increasing demand for sunglasses has resulted in a proliferation of designs for sunglasses. Thus some sunglasses are designed primarily to meet functional objectives; others are more stylish. Sunglasses which depart in structure and appearance from conventional spectacle-type sunglasses are disclosed in the following U.S. Pat. Nos.: Sameth, 2,491,137, Dec. 13, 1949, Eye Protector, in which is disclosed an eye protector or goggle which includes a one-piece plastic lens assembly consisting of two spaced apart lens portions connected by a bridge, forming a nose relief therebelow. Opposite upper corners of the two lens portions are notched to received a fabric attachment band, which is looped around the bridge section. The free ends of the band must be tied in a knot to secure the eye protector to the head of a wearer.

U.S. Pat. No. McBrayer, 3,378,851, Apr. 23, 1968, Soft Frame Adjustable Eyeglasses: Discloses eyeglasses intended to be folded up and packaged in emergency survival kits. The eyeglasses have a soft plastic frame provided with two lens-holding openings, and an elongated upper band having VELCRO fasteners at opposite ends thereof, for securing the band at various circumferences around the head of the wearer.

U.S. Pat. No. Jean, Jr., et al., 4,616,367, Oct. 14, 1986, Headband With Detachable Lenses: Discloses a headband having VELCRO fasteners at opposite ends thereof, and means for fastening a pair of lenses to the band which are movable laterally to accommodate an individual's inter-pupillary distance and also angularly to accommodate the individual's forehead angle.

U.S. Pat. No. Daigle, 4,712,254, Dec. 15, 1987, Headband and Eyepiece Combination: Discloses a flexible headband securable around the head of a wearer by VELCRO fasteners at opposite ends of the band. A pocket within the band holds a dual eyepiece assembly, which may be pulled down into an operable position over the eyes of a wearer, and re-inserted into the pocket when not in use.

U.S. Pat. No. Janusz, 4,811,430, Mar. 14, 1989, Eye Shield and Headband Combination: Discloses an endless flexible moisture-absorbent headband having a VELCRO strip on part of its eye shield inner surface. An eye shield consisting of two lens portions joined by a bridge to form a nose relief has a VELCRO strip adhered to the upper margin at its outer surface. The eye shield is storable within a pocket in the headband when not in use, and adherable to the VELCRO strip on the inside of the band when it is desired to have the eye shield extend below the band into an operative position.

U.S. Pat. No. Duggan, 4,852,189, Aug. 1, 1989, Headband Structure: Discloses a headband in the form of an endless loop made of moisture absorbing, expandable or stretchable material such as terrycloth or cheesecloth. A plastic eyeglass assembly having a VELCRO strip adhered to part of its inner perimeter is thus removably fastenable to the headband.

U.S. Pat. No. Could, D 207,187, Mar. 14, 1987, Combination Goggles and Headband: Discloses an ornamental design for goggles having an attached flexible headband.

U.S. Pat. No. Grayson, D 212,201, Sep. 10, 1968, Strap Support for a Pair of Spectacles: Discloses an ornamental design for a strip for spectacles, the design consisting of two straps, each having a loop at one end thereof for fastening to the free end of an eyeglass bow, and a VELCRO fastener at the other end thereof for fastening the two strips together at a desired longitudinal position.

The present invention was conceived of to provide sunglasses having structural and functional characteristics which constitute novel and non-obvious advancements in the art.

OBJECTS OF THE INVENTION

An object of the present invention is to provide an article of protective eye wear for humans which is self-buoyant, thereby allowing the article to be easily retrieved if inadvertently dropped into a body of water.

Another object of the invention is to provide improved sunglasses which are self-buoyant yet inherently light in weight.

Another object of the invention is to provide improved sunglasses of a single size which may be comfortably worn without modification on a wide range of head sizes.

Another object of the invention is to provide buoyant sunglasses which employ a minimum amount of fasteners, thereby affording an exterior appearance which is aesthetically satisfying and free of any protrusions that might impact a wearer during vigorous physical activity such as skiing.

Another object of the invention is to provide improved sunglasses having a small number of component parts.

Another object of the invention is to provide improved sunglasses requiring a small number of steps to manufacture.

Various other objects and advantages of the present invention, and its most novel features, will become apparent to those skilled in the art who peruse the accompanying specification, drawings and claims.

It is to be understood that although the invention disclosed herein is fully capable of achieving the objects and providing the advantages described, the characteristics of the invention described herein are merely illustrative of the preferred embodiment. Accordingly, we do not intend that the scope of our exclusive rights and privileges in the invention be limited to details of the embodiments described. We do intend that equivalents, adaptations and modifications of the invention reasonably inferable from the description contained herein be included within the scope of the invention as defined by the appended claims.

SUMMARY OF THE INVENTION

Briefly stated, the present invention comprehends an article of protective eye wear that possesses novel functional and structural characteristics which make the article particularly desirable for use by people engaging in sporting activities.

A basic embodiment of the protective eye wear according to the present invention consists of sunglasses which are self-buoyant. Thus, if the novel sunglasses according to the present invention are dropped into water, the sunglasses will float on the surface, allowing them to be easily retrieved.

The basic embodiment of the self-buoyant sunglasses according to the present invention includes an elongated strap having two rectangular end portions. The strap is fabricated from a synthetic low-density foam elastomer that forms a core, and a nylon-lycra fabric covering which is adhered to the core by the application of heat and pressure.

Midway between the two ends of the strap, the lower edge of the strap has an upwardly concave cutout that is symmetrically shaped and centered on the transverse center plane of the strap. A curved eye shield is attached at its upper margin to the inside edge. Of the narrowed portion of the strap above the cutout, that narrowed portion forming an outer eyebrow strip. An elongated flap continuous with the upper edge of the strap initially protrudes above the upper edge of the outer eyebrow strip. During manufacture of the sunglasses, the flap is folded down over the inner surface of the upper margin of the eye shield and is secured to the eye shield and inner surface of the strap, thereby forming an inner eyebrow strip which secures the eye shield in place. Adjustable fastening means, preferably loop and pile strips, are provided in the free ends of the strap, thereby permitting the strap to be wrapped around and fastened to heads of various diameters.

BRIEF DESCRIPTION OF THE DRAWINGS

FIG. 2 is a front elevation view of the article of FIG. 1.

FIG. 6 is a rear elevation view of the article of FIG. 1.

FIG. 9 is a fragmentary front elevation view of an alternate embodiment of the sunglasses of FIG. 1, showing a modification of a strap that is a component of the sunglasses.

DETAILED DESCRIPTION OF THE INVENTION

Figure 1:
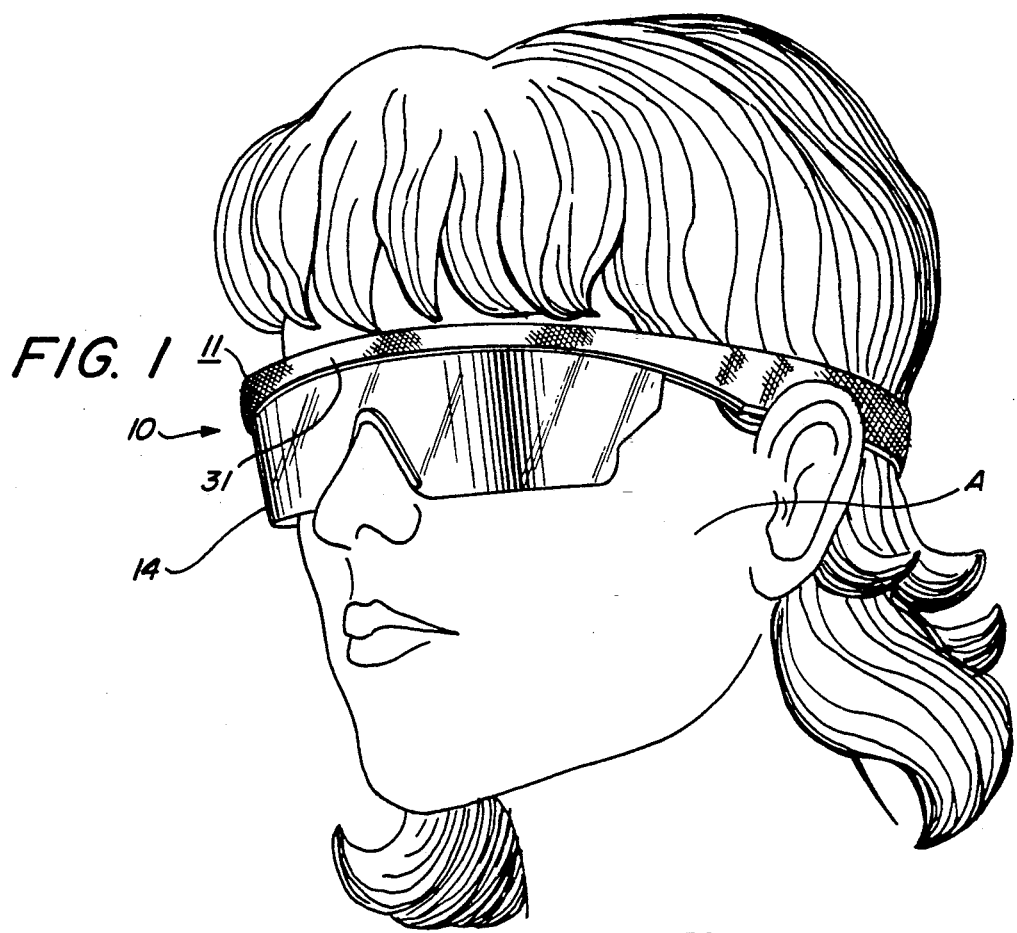
FIG. 1 is a perspective view of a novel buoyant wrap-around sunglass according to the present invention, showing the article attached to a person's head.

Referring now to FIGS. 1 through 8, novel buoyant wraparound sunglasses according to the present invention are shown. FIG. 1 shows sunglasses 10 according to the present invention wrapped around and secured to the head A of a wearer.

As may be seen best by referring to FIGS. 2 through 7, sunglasses 10 include an elongated rectangular strap 11 made of a flexible material. Strap 11 has in its lower edge wall 12 a crescent-shaped notch 13 that is symmetrically shaped and centered on the transverse midplane of the strap. An eye shield 14 having the shape of a thin, curved plate of generally uniform thickness is attached to strap 11, symmetrically positioned within notch 13, i.e., with the outer lateral edge walls 15 of the eye shield equidistant from the outer lateral edge walls 16 of strap 11. The manner of attachment of eye shield 14 to strap 11 is described in detail below.

As may be seen best by referring to FIGS. 2, 4, 5 and 6, eye shield 14 has in upper and lower plan views a shape which may be envisioned as a section cut from a thin-walled cylinder. Thus, eye shield 14 has a single axis of curvature located rearward of the eye shield, and may be described as a convex cylindrical lens. For use by people not requiring corrective lenses, outer surface 17 and inner surface 18 of eye shield 14 would be parallel, thereby neither diverging nor converging rays of light passing normally through the inner and outer surfaces of the eye shield.

In the preferred embodiment, eye shield 14 is so fabricated as to attenuate light incident upon outer surface 17 of the eye shield, thereby reducing discomforting glare from bright sunlight. Preferably, eye shield 14 substantially attenuates harmful rays of the sun which lie in the ultraviolet portion of the electromagnetic spectrum. Also, eye shield 14 should be constructed of a material which is durable, breakage resistant, and resistant to degradation by heat, cold, sunlight and water.

The present inventor has found that certain plastics, such as polycarbonates, are a suitable material from which to fabricate eye shield 14. Polycarbonates and other thermosetting or thermoplastics may be prepared in a variety of ways, well known in the art, to reduce the light transmitted through the material. Thus, eye shield 14 may be impregnated or coated with light absorbing dyes, or coated with light reflecting materials.

In the preferred embodiment of sunglasses 10, eye shield 14 is fabricated from polycarbonate plastic having a thickness in the approximate range of 1/16th inch ±1/64th inch. Preferably, the light transmissibility of eye shield 14 is reduced to a value of about 80 percent by applying a light reflecting coating consisting of titanium dioxide to outer surface 17 of the shield. The coating is applied by placing the eye shield into a vacuum chamber and evaporative-vapor depositing titanium dioxide or other suitable coating unto eye shield 14, to produce a "smoke" or iridescent appearance thereto. For applications in which sunglasses 10 are to be used only for protection against impact injury to the eyes, eye-shield 14 may be clear.

Figure 5:
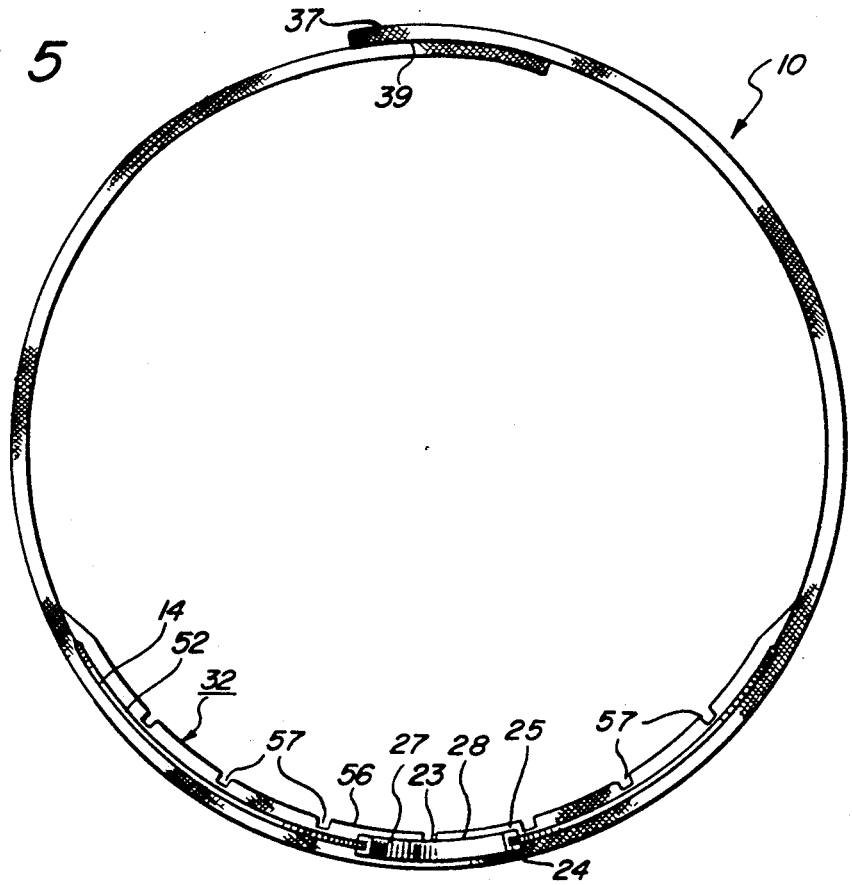
FIG. 5 is a lower plan view of the article of FIG. 1.

As may be seen best by referring to FIGS. 2 and 6, eye-shield 14 has in elevation view the shape of horizontally elongated sheet having a slightly convex upper edge wall 19, and a lower edge wall 20 of slightly greater convexity, i.e., of greater curvature. A nose-relief notch 21 having the shape of an inverted v is formed in lower edge wall 20 of eye shield 14, midway between the opposite transverse lateral side edge walls 15 of the eye shield. Nose relief notch 21 is of the proper size and shape to comfortably fit over noses of typical sizes. Preferably, as shown in FIGS. 5 and 6, a nose piece 23 is fitted into nose relief notch 21 to provide greater comfort to the wearer. Nose piece 23 has the general shape of a V-shaped channel bar having in its outer peripheral wall surface 26 a channel 25 adapted to insertably receive inner-facing edge walls 26 of notch 21. Nose piece 23 may be made from any suitable material, including plastics and elastomers. If made of a relatively hard plastic or other hard material, nose piece 23 preferably has attached to its inner wall surface 27 a V-shaped protrusion 28 made of an elastomer or other soft, resilient material adapted to rest comfortably on the nose of a wearer.

Figure 3:
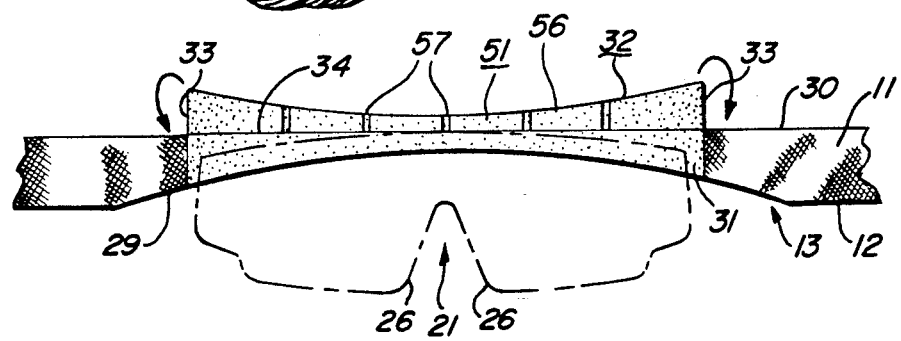
FIG. 3 is a fragmentary front elevation view of the article of FIG. 1, showing the article prior to attachment of a lens assembly shield that is a component of the sunglasses.

The novel means for attaching eye shield 14 of sunglasses 10 to strap 11 may be best understood by referring to FIGS. 3 though 6. FIG. 3 is a fragmentary view showing a part of strap 11 prior to attachment of eye shield 14 to the strap. As shown in FIG. 3, crescent-shaped notch 13 in lower edge wall 12 of strap 11 has a concave upper edge wall 29. Formed between upper edge wall 29 of notch 13 and upper edge wall 30 of strap 11 is an outer eyebrow strip 31. Outer eyebrow strip 31 has a minimum height at the transverse center plane of sunglasses 10, and tapers to the larger height of strap 11 near both lateral limits of notch 13.

Referring still to FIG. 3, strap 11 is seen to include an elongated, generally rectangular-shaped flap 32 that protrudes upwards from upper edge 30 of the strap, above outer eyebrow strip 31. Flap 32 has opposite lateral edge walls 33 which are equidistant from the transverse center plane of strap 11. Also, flap 32 is hingedly connected to upper edge 30 of strap 11 along a hinge line 34.

To attach eye shield 14 to strap 11, the eye shield is positioned behind the strap, with upper edge wall 19 of the eye shield aligned with hinge line 34, as shown in FIG. 2. Then, as shown in FIGS. 2 through 6, flap 32 is folded down on hinge line 34 behind inner surface 18 of eye shield 14, parallel to outer eyebrow strip 31, and secured thereto. Thus positioned, flap 32 forms an inner eyebrow strip.

In the preferred embodiment sunglasses 10 flap 32, which forms an inner eyebrow strip, outer eyebrow strip 31, and eyeshield 14 are secured to one another in a single operation, as follows. As shown in FIGS. 2 through 6, an outer strip 35 of tape coated on both sides with a pressure sensitive adhesive is cut into an outer preform having an outline shape approximating that of outer eyebrow strip 32 and adhered thereto, or to the upper margin of outer surface 17 of eyeshield 14. Also, an inner double-sided adhesive tape preform 36 having an outline shape approximating that of inner eyebrow flap 32 is adhered thereto, or to the upper margin of inner surface 18 of eyeshield 14. Eyeshield 14 is then positioned relative to strap 11 as was described above. Flap 32 is then folded downwards along hinge line 34. Inwardly directed compressive forces are then applied to the outer surfaces of outer eyebrow strip 31 and inner eyebrow strip, or flap, 32. These compressive forces cause the outer and inner pressure-sensitive tape preforms 35 and 36 to adhesively bond to the upper margins of outer and inner surfaces 17 and 18 of eyeshield 14, and to inner facing surfaces of outer and inner eyebrow strips 31 and 32, thus forming a laminated or "sandwiched" means for fastening the eyeshield to strap 11. The laminated fastening means just described provides a smooth and aesthetically satisfying exterior appearance, free from any protruding elements which might possibly injure a wearer during vigorous physical activity.

The sunglasses 10 according to the present invention include means for conveniently and quickly fastening and unfastening strap 11 around heads of various sizes. As may be seen best by referring to figure, a preferred fastening means for strap 11 includes an elongated rectangular strip 37 made of VELCRO-type hook material fastened to the inner surface 30 of strap 11, near an outer lateral edge wall 16a of the strap. Also, as shown in figure included in the means for fastening strap 11 is an elongated rectangular strip 39 of deep pile material having an array of looped strands engageable by hook strip 37. Loop strip 39 is fastened to the outer surface 40 of strap 11, near an outer lateral edge wall 16 b of the strap. Preferably, loop strip 39 is longer than hook strip 37, the ratio of lengths be determined by what range of head circumferences sunglasses 10 are intended to accommodate, as those skilled in the art will recognize. Strips 37 and 39 may be fastened to strap 11 by sewn threads 41, or by any other suitable means.

In the preferred embodiment of sunglasses 10, strap 11 is fabricated in a way that makes the sunglasses self-buoyant, as will now be described.

Referring now to FIG. 2 and FIGS. 4 through 7, but especially to the latter figure, strap 11 of self-buoyant sunglasses 10 may be seen to be a composite structure having a core section 42 and a covering 43. Core section 42 and covering 43 are chosen from materials which afford sufficient buoyancy to sunglasses 10 to cause the sunglasses to float, even when immersed in water for a substantially long time. The present inventors have found that a particularly suitable choice of materials for core section 42 and covering 43 are a low density (approximately 2 lb per cubic foot) closed density cell, crosslinked cell synthetic foam elastomer such as VOLARA brand polyethylene, and nylon LYCRA spandex, respectively. In the preferred embodiment polyethlene closed cell foam elastomer having a density in the approximate range of 2 lb per cubic foot ±15% is used for core 42. Also, in the preferred embodiment, cover 43 is fabricated from a 5 oz. nylon LYCRA spandex material. Preferably, the material of which cover 43 is fabricated is treated with a water repelling coating such as a silicone or fluoroaliphatic resin.

Figure 7:
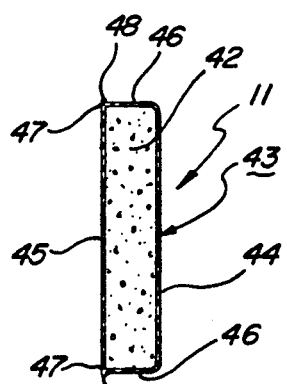
FIG. 7 is a transverse sectional view of the article of FIG. 1, taken along line 7—7 of FIG. 2.

As may be seen best by referring to FIG. 7, cover 43 is adhered to the outer surfaces of foam core 42. In the preferred embodiment, cover 43 comprises an upper strip 44 having the shape of an inverted U, and a lower flat strip 45. Upper strip 44 and lower strip 45 are bonded to foam core 42 by a process utilizing the combined effects of heat and pressure, a process referred to as thermal forming.

To bond nylon LYCRA cover 43 to foam core 42, one surface of the cover is passed across a flame, and then pressed into a block of foam. This process step adheres the LYCRA material to the foam, forming a laminated block. The laminated block is then placed in a lower rigid forming channel or die. The sides 46 of upper strip 44 of cover 43 are then pressed into contact with the sides of foam core 42 and with the longitudinal edges 47 of lower strip 45, preferably by use of an upper extrusion-type channel die. Pressure of about 1000 lbs. per square inch is then applied normal to upper strip 44 and lower strip 45, while heating the strips and foam core 42 to a temperature of about 300 degrees F. The stated values of heat and pressure are maintained for a period of about 75 seconds ±15 seconds. The thermal forming process results in upper strip 44 and lower strip 45 being securely adhered to foam core 42. Also, the thermal forming process causes sides 46 of upper LYCRA strip 43 to bond to longitudinal edges 47 of lower strip 45, forming longitudinally disposed seal%s 48.

Figure 8:
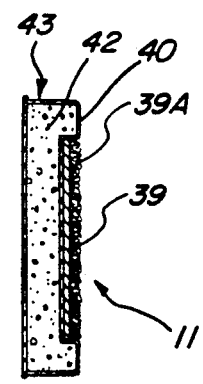
FIG. 8 is another transverse sectional view of the article of FIG. 1, taken along line 8—8 of FIG. 2.

Strap 11, thermally formed as described above, has a smooth, comfortable-to-wear exterior and a securely encapsulated, buoyant, resilient foam core. Preferably, that portion 39 of the fastening means used to fasten together the two free ends of strap 11 that lies on the outside of the strap is recessed with respect to outer surface 40 of the strap. Thus, as shown in FIGS. 2 and 8, a rectangular depression 39A is formed in the outer surfaces of foam core 42 and LYCRA cover 43, near an outer lateral end 16b of strap 11. Depression 39A is of the proper size and shape to receive deep-pile fastener strip 39. Thus positioned, the outer surface of the fastener strip is at or below outer surface 40 of strap 11, thereby affording a smooth and pleasing appearance to the exterior surface of sunglasses 10.

Figure 4:
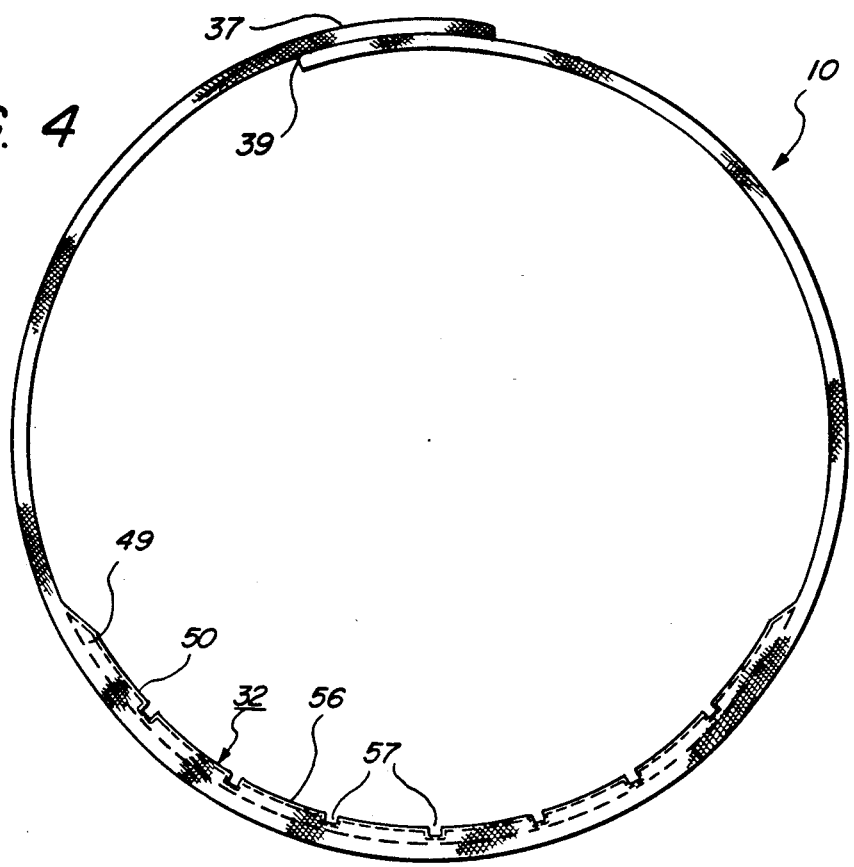
FIG. 4 is an upper plan view of the article of FIG. 1.

In the preferred embodiment of sunglasses 10, flap 32 forming an inner eyebrow strip is also made of a LYCRA-clad, or encapsulated foam core. Thus, as shown in FIGS. 3 through 5, flap 32 is preferably made of a wedge-shaped foam core 49 that is encapsulated by a LYCRA cover 50. Cover 50 has a U-cross section upper strip portion 51 and a lower flat strip portion 52. Upper strip portion 51 has a longitudinal edge hingedly joined to outer eyebrow strip 31 along longitudinally disposed hinge line 34, as shown in FIG. 3.

Cover 50 of flap 32 is preferably bonded to core 49 by the same type of thermal forming process described above for strap 11, desirably at the same time. As may be seen best by referring to FIGS. 4 through 6, rear surface 56 of flap 32 preferably has formed therein a plurality of vertically disposed grooves, spaced apart at regular intervals. Grooves 57 prevent bunching of cover strip 51 of flap 32, which might otherwise occur in response to longitudinally disposed compression forces, when flap 32 is concavely curved, as shown in FIGS. 4 and 5. Grooves 57, as well as performing a compression relieving function, provide air circulation paths between flap 32 and the brow of a wearer, increasing the wearing comfort of sunglasses 10.

FIG. 9 illustrates an alternate embodiment 60 of sunglasses 10. In the alternate embodiment 60 of sunglasses 10, lower edge wall 62 of strap 61 is provided with an arcuate ear relief notch 65.

What is claimed is:

1. An article of protective eye wear comprising:
   a. an elongated, thin flexible strap adapted to encircle and be retained on a human head, said strap having joined to the upper longitudinal edge thereof on a hinge line a flexible flap, said flap being adapted to fold downward on said hinge line and rearward of said strap, said strap having a lower longitudinal edge wall in which is formed a cutout having a concave edge and forming above said cutout edge an outer eyebrow strip or lesser height than the remainder of said strap.
   b. an eyeshield having the shape of a thin, arcuately curved plate, said eyeshield having an upper longitudinal edge wall shaped similarly to said hinge line, and having a circumferential width approximately equal to the circumferential width of said flap, and
   c. means for holding the upper margin of said eyeshield sandwiched between the inner facing surfaces of said folded-down flap and said strap, said means comprising in combination a first pressure sensitive adhesive layer between the inner surface of said folded-down flap and the rear surface of said upper margin of said eyeshield, and a second pressure sensitive adhesive layer between the inner surface of said strap and the front surface of said upper margin of said eyeshield.

2. The article of claim 1 wherein said flap is contiguous with said strap.
3. The article of claim 2 wherein said first pressure sensitive adhesive layer is further defined as a thin flexible substrate coated on both sides with a pressure sensitive adhesive.
4. The article of claim 2 wherein said second pressure sensitive layer is further defined as a thin flexible substrate coated on both sides with a pressure sensitive adhesive.
5. The article of claim 2 wherein said cutout is symmetrically shaped and located wit respect to a transverse mid-plane of said flap.
6. The article of claim 1 wherein the specific gravity of said article is less than one.
7. The article of claim 1 wherein said strap is further defined as comprising an elongated block of synthetic elastomeric foam having a cover made of a synthetic polymer fabric, said fabric cover comprising a first, lower elongated flat strip of said fabric and a second, upper elongated strip of said fabric having a U-shaped transverse cross-sectional shape, the longitudinal edges of said strips being thermally fused to one another and to the outer surfaces of said block of foam.
8. The article of claim 1 wherein said flap is further defined as having formed in the rear outer surface thereof a plurality of grooves.
9. An article of protective eye wear comprising:
   a. an elongated, thin, flexible strap, said strap being a composite laminated structure having a buoyant and resilient foam-core having a synthetic fabric covering thermally fused to the outer surfaces of said foam core to form an encapsulated structure, said strap having two generally rectangular shaped end portions, said strap having formed in the lower longitudinally disposed edge wall thereof cutout section having an arcuately shaped edge, said cutout section being symmetrically shaped about a transverse plane through said strap located approximately midway between the outer lateral edge walls of said strap, and forming an outer eyebrow strip,
   b. an eye shield having the shape of a thin, curved plate having a front surface and a rear surface extending substantially perpendicular to a human wearer's line of sight, the upper margin of which plate is contoured to fully cover a substantial portion of said arcuately shaped edge within said cutout,
   c. means for fastening said eye shield to said strap, wherein portions of at least one of said front and a rear surfaces abut said strap, and
   d. means for fastening said strap around the head of a human wearer with said eye shield positioned in front of the eyes of said wearer.
10. The article of claim 9 wherein said resilient core is further defined as being an elastomeric foam.
11. The article of claim 10 wherein said fabric covering si further defined as being water repellant.
12. The article of claim 10 wherein said synthetic polymer fabric covering is bonded to said elastomeric foam by the application of heat and pressure.
13. The article of claim 9 wherein said means for fastening said eye shield to said strap comprises;
   a. a flap formed in said strap, said flap protruding upwards from the upper longitudinal edge wall of said strap, and said flap being symmetrically located with respect to said cutout section in said lower edge wall of said strap, said flap being hingedly joined to the upper edge wall of said strap, said strap being adapted to fold down rearward of said strap, and b. means for securing said flap to the upper margin of said eye shield.

14. The article of claim 13 wherein said means for securing said folded down flap to said upper margin of said eye shield comprises a first layer between the rear inner surface of said flap and the rear surface of said upper margin of said eye shield.

15. The article of claim 14 further including a second adhesive layer between the rear surface of said outer eyebrow strip and the front surface of said upper margin of said eye shield.

16. The article of claim 15, wherein said means for fastening said strap around the head of a human wearer comprises in combination a first hook-type fabric fastener strip on a surface of a first end portion of said strap, said hook-type fabric fastener being located near the outer lateral end wall of said first end portion of said strap, and a second, loop-pile type fabric fastener strip on an opposite surface of the opposite end portion of said strap.

17. The article of claim 16 wherein said resilient core of said strap is of sufficient buoyancy to make said article selfbuoyant.

18. The article of claim 17 further including in said lower edge wall of each of said end portions of said strap, intermediate said cutout section and said lateral end of strap, an arcuately shaped notch adapted to fit over the ear of a wearer.

19. The article of claim 13 wherein the rear surface of said folded-down flap is provided with a plurality of grooves adapted to provide ventilating air spaces between said surface and the head of a wearer.

* * * * *